United States Patent [19]

Pauley

[11] 4,241,731
[45] Dec. 30, 1980

[54] UNIVERSAL ARM SUPPORT

[76] Inventor: James H. Pauley, Rte. 1, Box 251, Ripley, W. Va. 25271

[21] Appl. No.: 905,088

[22] Filed: May 11, 1978

[51] Int. Cl.³ .............................................. A61F 5/40
[52] U.S. Cl. ................................................... 128/94
[58] Field of Search ..................... 128/87 R, 84 C, 85, 128/88, 94; 403/53, 58, 82, 87, 90

[56] References Cited

U.S. PATENT DOCUMENTS

| | | | |
|---|---|---|---|
| 1,202,698 | 10/1916 | Ford | 403/90 |
| 1,639,815 | 8/1927 | Siebrandt | 128/88 |
| 2,172,178 | 9/1939 | Rosenberg | 128/85 |
| 2,361,102 | 10/1944 | Horne | 128/94 |
| 3,843,083 | 10/1973 | Angibaud | 403/90 |

FOREIGN PATENT DOCUMENTS 1280471 10/1968 Fed. Rep. of Germany ........ 128/87 R
44445 6/1961 Poland ..................... 128/88

OTHER PUBLICATIONS

Catalog, Orthopedic Equipment, Inc. Bourbon, Ind. 46504, Aeroplane Splint pp. 163-164 copyright 1969.

Primary Examiner—Robert W. Michell
Assistant Examiner—J. L. Kruter
Attorney, Agent, or Firm—Jim Zegeer

[57] ABSTRACT

A universal arm support or brace is disclosed which is constituted by a half moon or arcuate shaped waist-engaging member secured to the body of the user by a belt and two metal rods supported on the waist-engaging member for angular adjustment relative thereto, extend upwardly to a further arcuate shaped saddle assembly which fits under the upper arm of the user just above the elbow and between the elbow and the shoulder. Each of the stanchions is constituted by a telescoping arrangement which permits adjusting the height of the saddle assembly relative to the waist-engaging member. A first attachment is adjustably secured at the upper end of the stanchions just below and to the saddle assembly and extends outwardly therefrom and has at the remote end a small elbow platform for supporting the user's elbow; a forearm plate is hingedly secured to the elbow platform. A second attachment secured to the saddle by a threaded shaft has a right-angle support for supporting the arm and hand of the user and it is adjustably secured along the supporting arm by a wing nut. The saddle member is constituted by a slitted arcuate tube which has a saddle carrier or slide therein to thereby permit rotation of the saddle relative to the arm support bracket, thereby permitting rotation of the forearm support so that it may be used during times when the patient is lying down. A key feature of the invention is that it is easily adaptable to all user positions so that at all times the arm of the user may be held in an elevated position, and can accommodate both children and adults.

7 Claims, 11 Drawing Figures

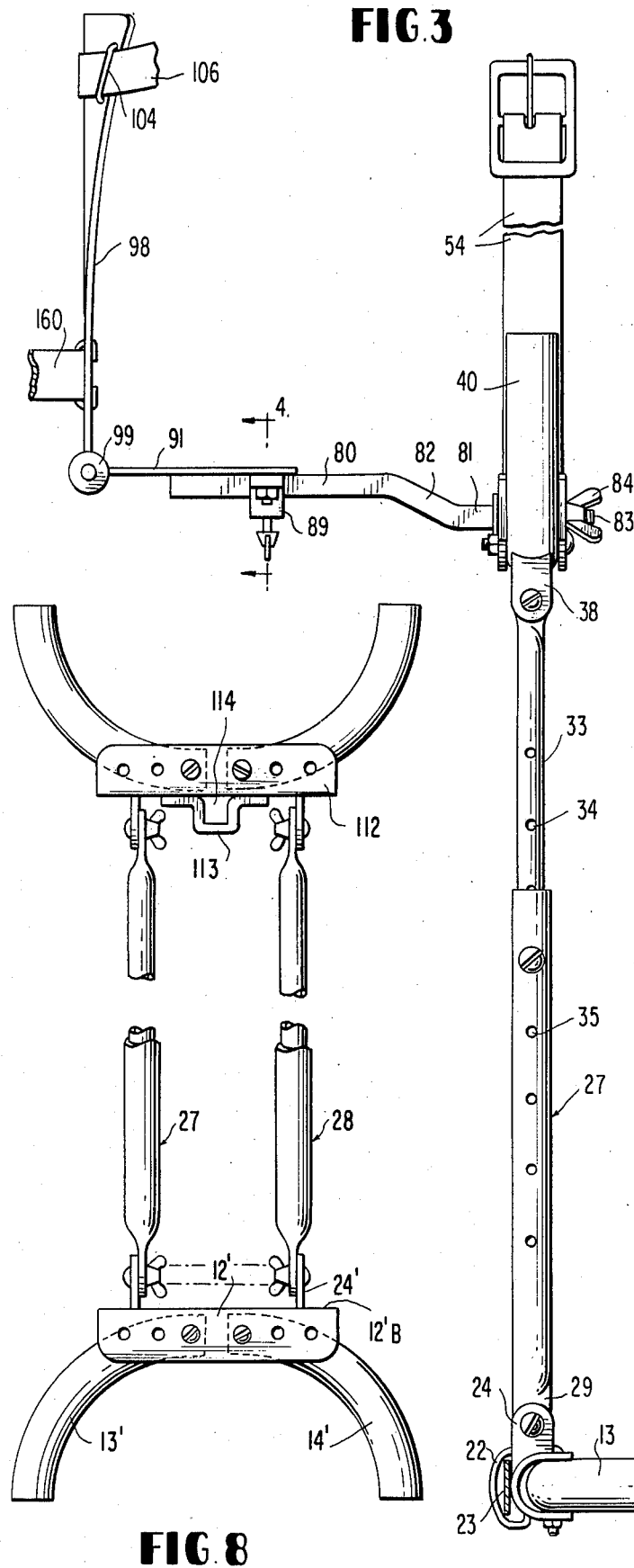
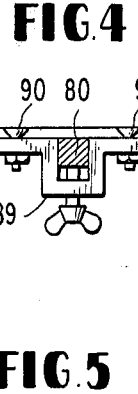

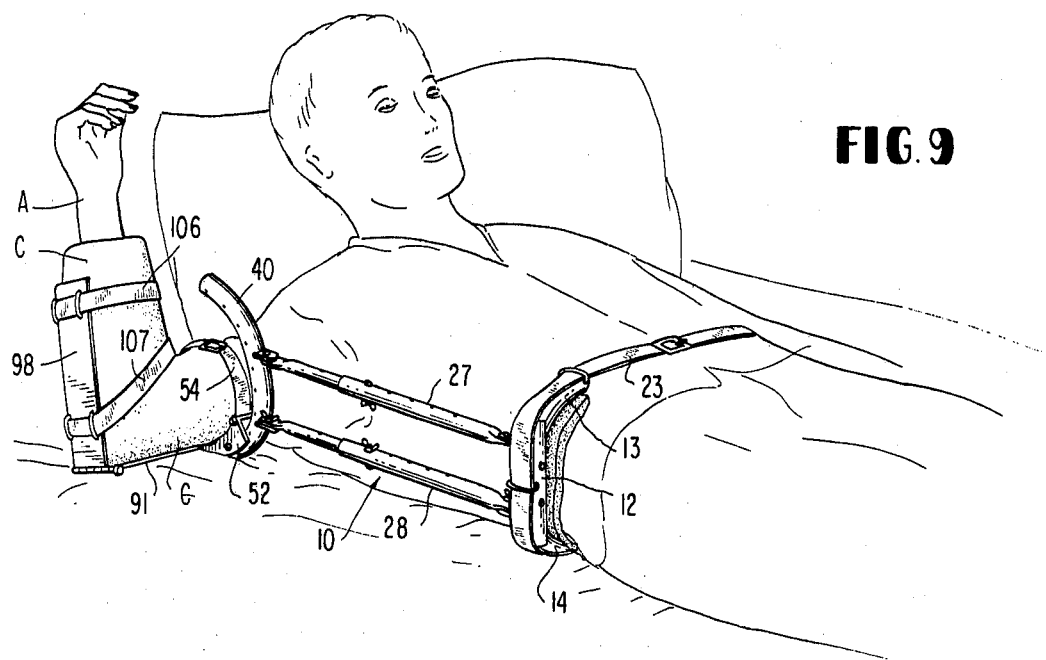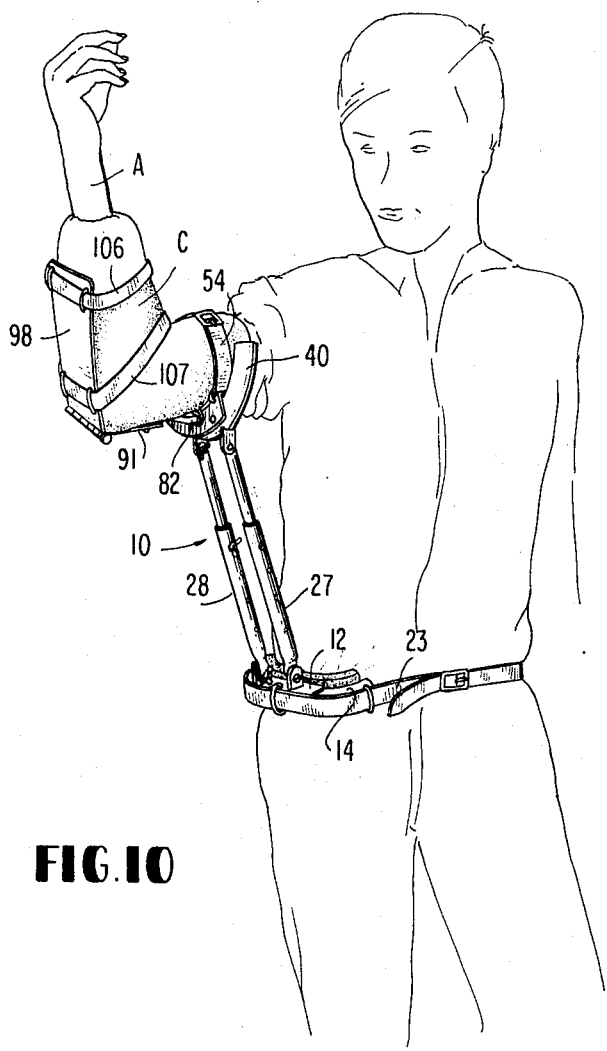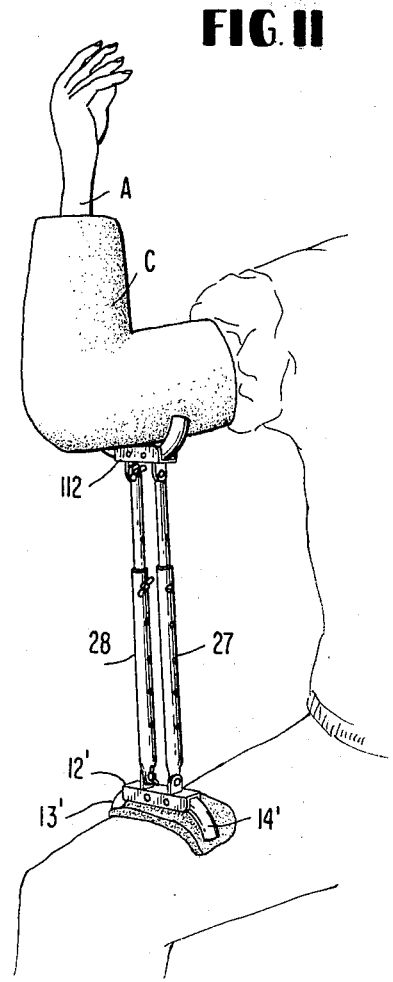

UNIVERSAL ARM SUPPORT

BACKGROUND AND BRIEF DESCRIPTION OF THE INVENTION

The present invention is directed to a novel device for supporting a fractured immobilized arm which permits the arm to be placed in the optimum position to permit both rapid restoration of function to the whole patient as well as to the terminal portion of the injured arm.

On numerous occasions, doctors have been frustrated at the end result of a fractured forearm or other part of the arm that either failed or is unnecessarily delayed in regaining full recovery because of the dependent edema and its sequelae. The economic loss to the patient is immense. They not only have a physical impediment prohibitive of returning to a useful occupational level, but encounter the added expenses of physiotherapy, additional functional splinting, etc. In order to avoid these disastrous complications, the treatment prescribed by doctors is to maintain elevation of the injured part, preferably above the level of the heart until the period of swelling, cast pressure necessary to maintain reduction, and accute inflammatory changes, have subsided. The joints of the hand are extremely sensitive and severely impaired by the slightest amount of swelling. Patients often find it difficult to carry the arm up in the air, and frequently fail to understand the implications of not doing so and often experience shoulder problems if they do. At the present time, the art has not produced any popular, universally recognized splint to supplement the fracture care of the upper extremities and assist in avoiding the tragic consequences referred to above. In the prior art, there are a number of upper arm support devices which are primarily designed for definitive fracture reduction and care. Such devices are disclosed in U.S. Pat. No. 1,257,297, issued to F. B. Brown in 1918 entitled "Arm and Shoulder Brace", U.S. Pat. No. 1,340,630, issued to R. D. Maddox in 1920 and entitled "Arm Abduction Splint", U.S. Pat. No. 3,952,733 issued to E. B. Williams in 1976 and entitled "Arm Support", U.S. Pat. No. 2,010,328, issued to J. R. Siebrandt in 1935 entitled "Surgical Splint Appliance", U.S. Pat. No. 2,191,283, issued to E. E. Longfellow in 1940 entitled "Splint", U.S. Pat. No. 2,310,566, issued to R. Anderson in 1943 entitled "Clavicle Splint", U.S. Pat. No. 1,921,987, issued to J. J. Ettinger in 1933 entitled "Surgical Splint", U.S. Pat. No. 1,961,118, issued to J. J. Ettinger in 1934 entitled "Surgical Splint", and U.S. Pat. No. 890,842, issued to R. H. Cheatham entitled "Clavicular Apparatus". Thus, it will be seen that Cheatham (issued in 1908), Brown (issued in 1918), Longfellow (issued in 1938) and two Anderson patents (issued in 1937 and 1939, respectively) are primarily designed for definitive fracture reduction and care. By necessity these are relatively complicated devices that a patient could not and should not adjust. The present splint is simple and can be adjusted by the patient as his or her spatial relationships to gravity indicate, such as standing, sitting or lying. The relatively more recent patent of Williams (issued in 1976) lacks flexibility for elbow position, does not support the proximal posterior forearm and has a fixed relationship to the trunk.

The present invention is directed to a universal splint or brace constructed of light-weight material. The ease of application, adjustment and adaptability are clear and concise. It can be quickly set to fit any patient. It includes rotation of the arm support to maintain the injured limb up in the air when the patient is in the supine or lying position—a new and invaluable concept. Total support on the trunk eliminates undue pressure in the axilla (armpit) over the arteries and nerves. The patient can be properly ambulated, yet painlessly and, more importantly, without effort, and even unconsciously maintain a static elevation of the injured part in the necessary and proper positions to avoid edema and its complications and thereby expediting regaining full functional recovery by the patient.

The object of the present invention is to provide a universal arm brace or splint for supporting an immobilized upper extremity or arm which avoids the disabling and painful complications and one wherein the patient can be properly ambulated and yet painlessly and unconsciously provided with a device for maintaining static elevation of the injured arm part, preferably above the level of the heat until the period of swelling and cast pressure necessary to maintain reduction and accute inflammatory changes have subsided.

The above and other objects, advantages and features of the invention will become more apparent when considered in conjunction with the following specification and accompanying drawings wherein:

BRIEF DESCRIPTION OF THE DRAWINGS

FIG. 3 is a side elevational view of the arm brace shown in FIG. 2;

FIG. 4 is a cross-sectional view taken along the arrows 4—4 of FIG. 3;

FIG. 5 is a partial cross-sectional view taken through the saddle area of the arm brace shown in FIG. 3;

FIG. 6 is a cross-sectional view taken on lines 6—6 of FIG. 5 showing the internal saddle carrier;

FIG. 7 is a partial sectional view showing the locking arrangement for the angular adjustments at the ends of the stanchions:

FIG. 8 is a side elevational view of a modification of the lower assembly, its particular use in this mode being illustrated in FIG. 11;

FIG. 9 illustrates the invention as applied to a patient who is in the supine or lying position;

FIG. 10 illustrates the invention as applied to a patient in the standing or ambulatory position; and FIG. 11 illustrates the use of a sub-combination part of the invention to support the arm of the user while in a sitting position as at eating, chatting, or at toilet.

Referring now to FIG. 1, the universal brace or splint is constituted by two main assemblies, namely, lower assembly 10 and upper assembly 11. Lower assembly 10 includes a lower U-shaped bracket 12 and a pair of short arcuate members 13 and 14, respectively. Bracket 12 is a U-shaped member with a line of apertures 16 aligned in the legs of the U-shaped bracket member 12 for pivotably and adjustably securing the end 17 of arcuate member 13 therein. A similar series of aligned apertures 18 is provided for pivotally and adjustably securing the end 19 of arcuate member 14 therein. The ends 17 and 19 of the arcuate members 13 and 14, respectively, have apertures through which a removable fastener such as screws 20 or 21 are passed. It will be appreciated that cotterless clevis pins may be used in place of the screws 20 and 21. The positive self-locking security of the cotterless clevis pins have a locking ball mechanism (not shown) and come in various sizes and may be obtained under the trademark LEITZKE sold by that company of the same name. Belt loops 22 are provided in the outer ends of arcuate members 13 and 14 and proximate the center of U-shaped bracket 12 and receive and maintain a belt 23 as shown in FIG. 2 in position.

Figures 1, 2:
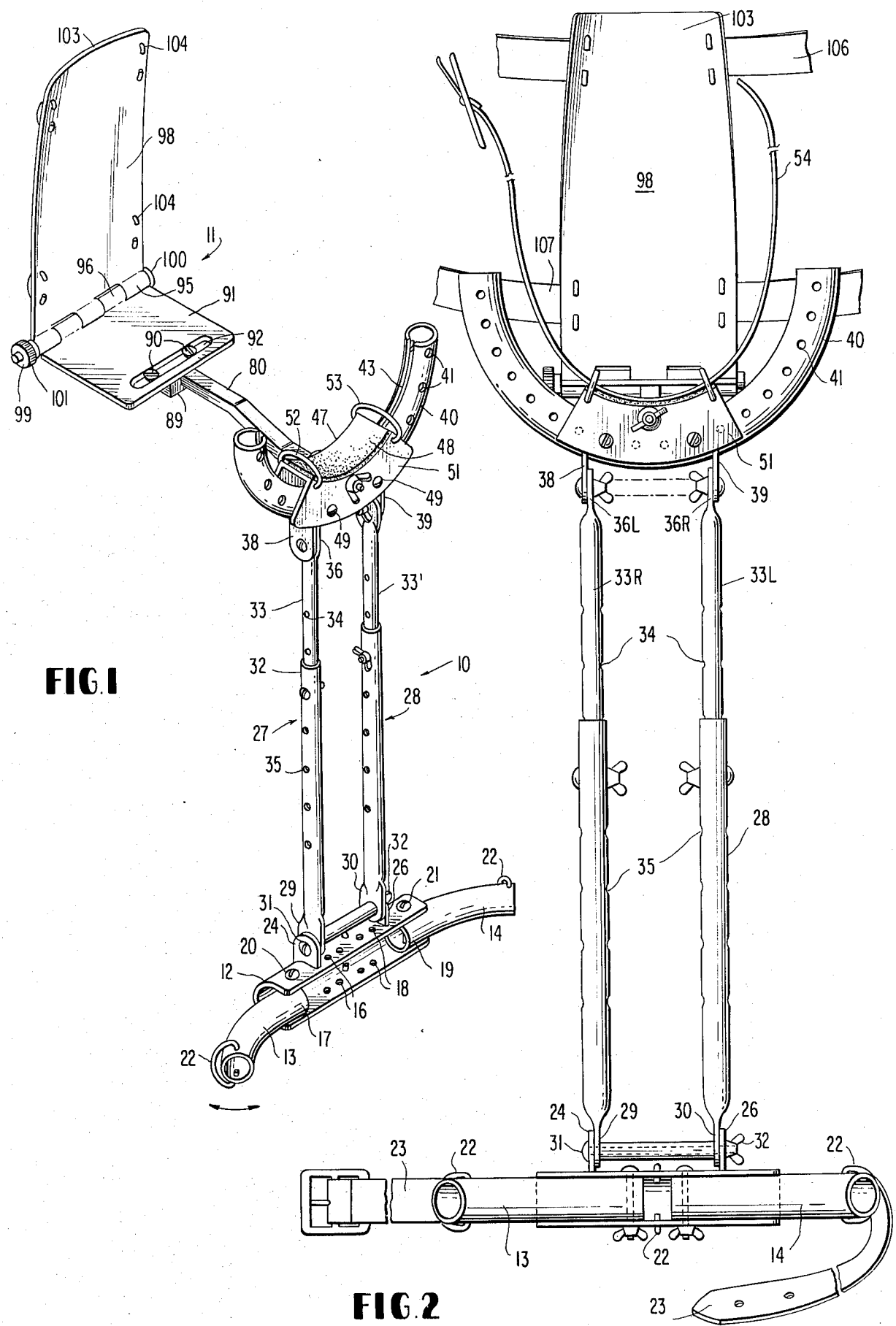
FIG. 1 is an isometric view of an arm brace or splint incorporating the invention.
FIG. 2 is an end view of the device shown in FIG. 1 in which the securing belts are shown attached.

On the upper outer surface of bracket 12 is a pair of spaced lugs 24, 26 which form clevis or hinge elements for supporting stanchions 27, 28, respectively. The stanchions 27, 28 are provided at their lower ends with enlarged hinge elements 29 and 30. The facing surfaces between hinge elements 29 and 24 and 30 and 26, respectively, are shown in FIG. 7 as being a series of matching embossments or teeth and grooves so that the stanchions 27 and 28 can be positioned at any desired angular position and locked in position by fasteners or screws 31 and 32, respectively, which are provided with wing nut fasteners 31 and 32. It will be appreciated that instead of two wing nuts, an elongated shaft or bolt may pass through both hinge elements (24, 29, and 26, 30) with a tubular rod positioned between the inner faces of stanchion hinge elements 29 and 30 so that a single tightening of a wing nut on the outside of one of the lugs 24 and 26 locks the stanchions in any adjusted angular position.

Stanchions 27 and 28 include telescoping members 33 and 33', each of which has a series of aligned adjustment holes, 34, 35 therein. The apertures or holes receive fastener members such as the screws illustrated or they may be cotterless clevis pins sold by the Leitzke Company. It will also be appreciated that a single wing nut adjustment may be used by aligning the apertures in telescoping part 33 with tube 32 of the stanchions 27 and 28 so as to reduce the number of parts used. The upper end of telescoping tube 33 includes a further hinge element 36, there being a hinge element on each telescoping tube or rod 33. Depending hinge parts or lugs 38 and 39 are formed on arcuate saddle member 40 and are secured thereto as by welding a 5" diameter saddle for small to med. arms, a 7 to 7½" saddle for large to extra large arms or casts. A hinge pin fastening assembly similar to the fastening assembly for hinge elements 24, 29 and 26, 30 is used for hinge elements 36, 38 and 39 so that the angular relationship between the stanchion elements 27, 28 can be easily effected so as to form a secure angular relationship between the stanchion and the saddle member 40. By reference to FIG. 7, the internal mating surfaces of the hinge elements are provided with embossments and notches or grooves so as to assure the fixed angular relationship once the fasteners are in place.

Arcuate saddle member 40 has a slot 43 formed on the internal radius thereof, and a saddle carrier member 44 (see FIGS. 5 and 6) travels inside of the arcuate saddle member 40. Saddle carrier 44 is formed with upstanding connectors 46 which project through slot 43 and are secured to a U-shaped arcuate saddle 47 which has a relatively broad arcuate cast-engaging saddle surface 48. To saddle surface 48 a non skip rubber pad can be used to prevent saddle from slipping when not using belts. A pair of fastening pins 49 pass through aligned apertures formed in the depending side walls or legs 51, 52 (See FIG. 6) so that the bracket or saddle member 47 can be adjustably secured along an arc to accommodate the supine or lying position of the user as shown in FIG. 9. In addition, the saddle member 47 has a pair of belt loops 52, 53 thereon for belt 54 (see FIG. 2). As shown in FIGS. 5 and 6, the carrier 44 has an upwardly extending projection or pair of connectors 46 which are welded or otherwise secured to the internal surface on the backside of the arcuate saddle element 48. Cotterless clevis pins 61, 62 projecting through apertures in the depending legs 51, 52 of saddle member 47 and through holes 41 and the opposite sides of arcuate member 40, lock the saddle member 47 in a fixed position along the arcuate track defined by slot 43 and arcuate member 40. As shown in FIG. 9, the carrier is rotated to permit the user to lie in a horizontal or supine position with the arm resting in saddle member 48.

ELBOW AND FOREARM SUPPORT ASSEMBLY

The elbow and forearm support assembly 11 has a rigid bar-arm element 80 which has a mounting end 81 connected by an offset portion 82 to the main portion theron. End 81 has a threaded end 83 on which is threadably mounted a wing nut 84. End 81 extends through a pair of aligned apertures or holes 86, 87 in legs or walls 51, 52 of the saddle member 47 (see FIG. 6) and is provided with a flange or a boss 88 which limits the movement of the end 81 or arm 80 so that upon tightening of the wing nut 84, the arm 80 is locked or secured against rotation about the axis thereof. It will be appreciated that instead of a round end 81 a square or other cross-sectional configuration may be used provided it is capable of being rotated about 90° (more or less, depending on the rotation of saddle 47 and carrier 44 in saddle member 40) to accommodate the supine position of the user and maintain the injured body part in the desired elevated condition. Rod 80 is received in a square bracket 89 which is secured by countersunk fasteners 90 in the lower underside surface of elbow support plate 91. Fasteners 90 are countersunk in slot 92 which permit a lateral adjustment of the elbow support 91 (as shown in FIG. 4, the elbow support 91 may be adjusted to the right or to the left of the axial center of rod 80). The outermost end of elbow support plate 91 is provided with a hinge half 95 which coacts with hinge half 96 formed in the forearm support 98. A locking screw 99, included as a part of the hinge pin 100, has a knurled circumference 101 which, upon tightening thereof, secures the hinge against rotation. This permits, if desired, angular adjustment of forearm plate 98 relative to arm support 91.

Plate 98 is slightly arcuate at the upper end 103 to accommodate curvature in the cast or arm of the user. In addition, belt loops 104 are provided at the upper and lower ends of plate 98 to receive securing straps 106 and 107 for securing the user's arm thereto. It will be appreciated that VELCRO fasteners may be provided at the ends of the belts or straps.

As shown in FIG. 8, the lower assembly 10 may be disengaged from the upper support assembly 11 for use in the manner illustrated in FIG. 11. However, FIG. 8 also discloses a modification in which there is a modification of the connection of offset rod extension 81 to the underside of the saddle assembly. In this embodiment, the lower arcuate elements 13' and 14' are duplicated at the opposite ends of the stanchion members 27, 28 and are pivotally secured to bracket 112 which is similar to bracket 12'. In this case, bracket 112 is a rectangular U-shaped configuration and has on the lower side thereof a securing bracket 113. Bracket 113 is welded or otherwise secured to the underside of bracket 112 and has a rectangular opening 114 therein which is adapted to receive the square offset end 81 of arm 80. In this embodiment, the rod 80 is secured by a wing nut screw (not shown) within the opening 114. In order for this modification to accommodate the supporting of an arm in an upraised position while the user is lying down, the offset rod end 81 is withdrawn from opening 114 and turned 90°, reinserted into a leg of the lower bracket member 12', hinge or lug parts 24' and 26' are on the base 12'B of the bracket 12'. However, the load carrying capacity and adaptability to the trunk or body of the user is essentially the same.

Referring now to FIG. 9, the user is shown lying down in a supine position. The lower assembly 10 is shown in a horizonal position with the lower arcuate members 13, 14 adjacent the body of the user and strap or belt 23 holding same in place. Arcuate members 13 and 14 are relatively short and, in the preferred embodiment, do not extend enough behind the user's back as to be uncomfortable, or press into the user's back in the supine or lying position. Saddle member 48 and its carrier 46 have been rotated to the position shown in FIG. 9. In addition, arm 80 has been rotated approximately 90° so that arm support plate 91 is in a substantially horizontal orientation and the support plate 98 is in a substantially vertical position. Straps 106 secure the arm A of the user in its cast C in a position such that the immobilized limb or arm is maintained substantially in the position shown, it being understood that other angular relationships can be maintained if desired. This maintains the arm in an elevated position to prevent swelling when the patient is lying down and is especially beneficial in keeping the injured part of the forearm and/or hand elevated during any periods of sleep, the belts maintaining the arm secured in a proper position to avoid movement of the splint or brace accidentally during sleep. The offset rod 80 is secured firmly in position in its carrier so that it does not rotate to thereby shift the position of the user's arm relative to the desired immobilized position above the level of the heart.

In FIG. 10, the trunk engaging element of the lower assembly 10 is shown secured by belt or strap 23 to the waist of the user whereas the upper saddle member is secured to the cast element beyond the armpit and between the armpit and the elbow. In this manner, total support is on the trunk of the user, the saddle assembly engaging the cast C on the upper arm between the elbow and armpit, and this eliminates undue pressure in the axilla over the arteries and nerves.

Referring now to FIG. 11, the upper assembly 11 has been removed and the upper and lower brackets adjusted angularly so that the stanchions 27 and 28 are substantially vertically extending from bracket 12' and the arcuate members 13', 14', which in the normal use are padded, rest upon the user's thigh or knee. The upper saddle area 47 is mounted on the upper ends of stanchions 27 and 28. The length of stanchions 27 and 28 is adjusted to comfortably accommodate the particular user's body, and maintain the injured part in a position for more rapid healing of the injured part of the user.

Thus, the brace of the present invention fits practically any size body or arm and it can be worn on either side or both sides simultaneously. It is versatile, requires only a small amount of body contact and can be worn over the user's clothing. The straps can be removed, along with the elbow and forearm support and to set the brace on the hip, or lay the arm in the upper half moon. For bathing in a bathtub, the lower part of the lower assembly 10 may be braced on the tub and the arm rested in the upper half moon. For eating at the table, the lower part may be set on the lap or thigh of the person and the arm rested in the upper half moon.

Preferably, the brace is made of light-weight aluminum parts except for the offset rod wing nut which may be made of steel or, preferably, light-weight high strength metal alloys.

The offset in the support arm 80 raises the arm above the saddle to avoid too much pressure on the main artery in the arm and thus allows the arm to rest on the elbow support which is another advantageous feature. Just above the elbow the arm saddle is adjustable to accommodate large or small arms or larger or smaller casts as the case may be. Moreover, this element pivots forward and aft to accommodate the particular muscular orientation of the individual. The hinge between plates 91 and 98 acts like a door hinge and adjusts in several positions from a vertical to horizontal depending on the angle of the cast or on the arm and, of couse, as noted above, the offset rod or arm can be moved inwardly or outwardly to accommodate differing lengths of arms of users. All parts connected to the body can be padded for comfort after the brace is adjusted to a particular body. The brace can be worn without belts or elbow support for casual use, such as going to the bathroom, etc. In all cases, the arm is held in a rigid position as prescribed by the physician, especially in the first 10-14 days after an arm is broken or immobilized. As the arm of the patient must be elevated to prevent swelling when the patient is in bed (which may be a large percentage of the time), the brace of this invention is especially beneficial to keep the arm elevated during the periods of sleep or supine conditions, thereby avoiding the disastrous complications that come about through edema and the consequences thereof. The present invention being constructed of light-weight materials and being easily adjusted to adapt itself to any size patient and use as disclosed herein is universally adjustable to supplement the fracture care of the upper extremities and assist in avoiding the tragic consequences referred to above. The present invention, supporting as it does, the proximal posterior forearm in a fixed relationship to the trunk of the user and always in a vertical position above the heart, provides distinct and necessary refinements and improvements not heretofore encompassed by the prior art. The present device possesses the necessary attributes to fulfill the need of both the practicing physician and the patient both of whom profit from fracture union unmarred by disabling, painful, and yet preventable, complications.

The above-disclosed embodiments are the preferred embodiments of the invention but it will be appreciated that those skilled in the art will be able to devise other modifications and improvements to the invention without departing from the spirit and scope of the claims appended hereto.

What is claimed is:

1. A universal arm brace adapted to support the fractured immobilized upper body limb or extremity of a person comprising,
a first arcuate means for engaging the trunk of the user for transferring substantially all load supported by said brace when the user is standing to the hip of the user and means securing said first arcuate means to the trunk of the user
a stanchion elongated means, a second arcuate means for engaging the arm of the user approximately midway of the elbow and the armpit of the user to thereby avoid undue pressure on blood vessels and nerves in the axilla of the user, means pivotly directly engaging and securing the respective ends of said stanchion means to one each of said first and second arcuate means, respectively, a forearm-elbow egaging means and means securing said forearm-elbow engaging means to the user's forearm-elbow, and means for rotatably and lockably supporting said forearm-elbow engaging means on said second arcuate means about a horizontal axis which is transverse to an axis through the trunk of the user to maintain the fractured upper body limb or extremity of the person in an elevated position above the heart when said person is alternately standing, sitting or lying in a supine position.

2. The universal arm brace defined in claim 1 wherein said trunk engaging first arcuate means is constituted by a pair of arcuate tube elements, a connecting element and means securing said pair of arcuate tubular members in different positions to said connecting element to adapt the said first arcuate member for trunk of different size users.

3. The universal arm brace defined in claim 2 wherein each said arcuate tube element is short such that when said arcuate trunk engaging assembly is affixed to the user and the user is in the supine position, which ever side of the user the brace is on said arcuate tubes are not beneath the user's back to create untoward discomfort.

4. The universal arm brace defined in claim 1 wherein said length adjustable stanchion means includes a pair of tube and telescoping rod assemblies each tube and rod assembly having apertures therein and pin means passing through aligned aperture pairs of said tube and telescoping rods to securing said stanchion means at a selected length.

5. The universal arm brace defined in claim 1 wherein said means rotatably and lockably supporting said forearm-elbow engaging means on said second arcuate means includes a saddle element moveable along an arc on said second arcuate means, and means securing said forearm-elbow engaging member on said saddle element for lockable rotary adjustment about said horizontal axis transverse to an axis through the trunk of the user.

6. The universal arm brace defined in claim 5 wherein said second arcuate means is tubular and has a slot on the inner radius thereof, said saddle element having a carrier portion mounted for movement within said second arcuate means and having a and including means for locking said carrier at a selected one of a plurality of positions.

7. The universal arm support defined in claim 1 wherein said elbow-forearm means includes a pair of plate members and locking hinge means joining said plate members together.

* * * * *